United States Patent [19]
Moss

[11] Patent Number: 4,543,089
[45] Date of Patent: Sep. 24, 1985

[54] GASTROINTESTINAL FEEDING AND ASPIRATING DEVICE FOR USE IN TREATING PATIENTS

[76] Inventor: Gerald Moss, R.D. #1, West Sand Lake, N.Y. 12196

[21] Appl. No.: 585,632

[22] Filed: Mar. 8, 1984

Related U.S. Application Data

[63] Continuation-in-part of Ser. No. 312,125, Oct. 16, 1981, abandoned.

[51] Int. Cl.⁴ .............................................. A61M 11/00
[52] U.S. Cl. ..................................................... 604/93
[58] Field of Search ....................... 604/93, 94, 96, 97, 604/102

[56] References Cited

U.S. PATENT DOCUMENTS 3,495,595  2/1970  Soper ............................. 128/350 R
3,771,527  11/1973 Ruisi .............................. 128/350 R
3,780,740  12/1973 Rhea .............................. 128/350 R
4,057,065  11/1977 Thow .............................. 128/349 B
4,114,625  9/1978  Onat ..................................... 128/348
4,364,394  12/1982 Wilkinson ............................ 604/96

OTHER PUBLICATIONS

"Abdominal Decompression: Increased Efficiency by Esophageal Aspiration Utilizing a New Nasogastric Tube", Moss et al., Amer. Journal of Surgery, vol. 133, New York, N.Y., Feb. 1977.

"Concise Guide to Biomedical Polymers", Boretos, Charles C. Thomas, Springfield, Ill., pp. 12-14, 64-65, 1973.

Primary Examiner—Stephen C. Pellegrino
Assistant Examiner—J. L. Kruter
Attorney, Agent, or Firm—Schmeiser & Morelle

[57] ABSTRACT

A gastrointestinal feeding and aspirating device and method for use in treating patients. The device comprises an aspirating lumen, a feeding lumen, and an inflation lumen. When properly disposed within the patient's body, orifices in the aspirating lumen are positioned within the stomach and the proximal segment of the small bowel. The orifice in the feeding lumen opens at a site which is also in the proximal segment of the small bowel, but is further downstream than the aspirating orifices. The inflation lumen communicates with a balloon which is inflated after the insertion of the device in order to help maintain the device in its proper position. In an alternate embodiment of the invention, a fourth lumen is added for the sole purpose of aspirating the stomach.

13 Claims, 4 Drawing Figures

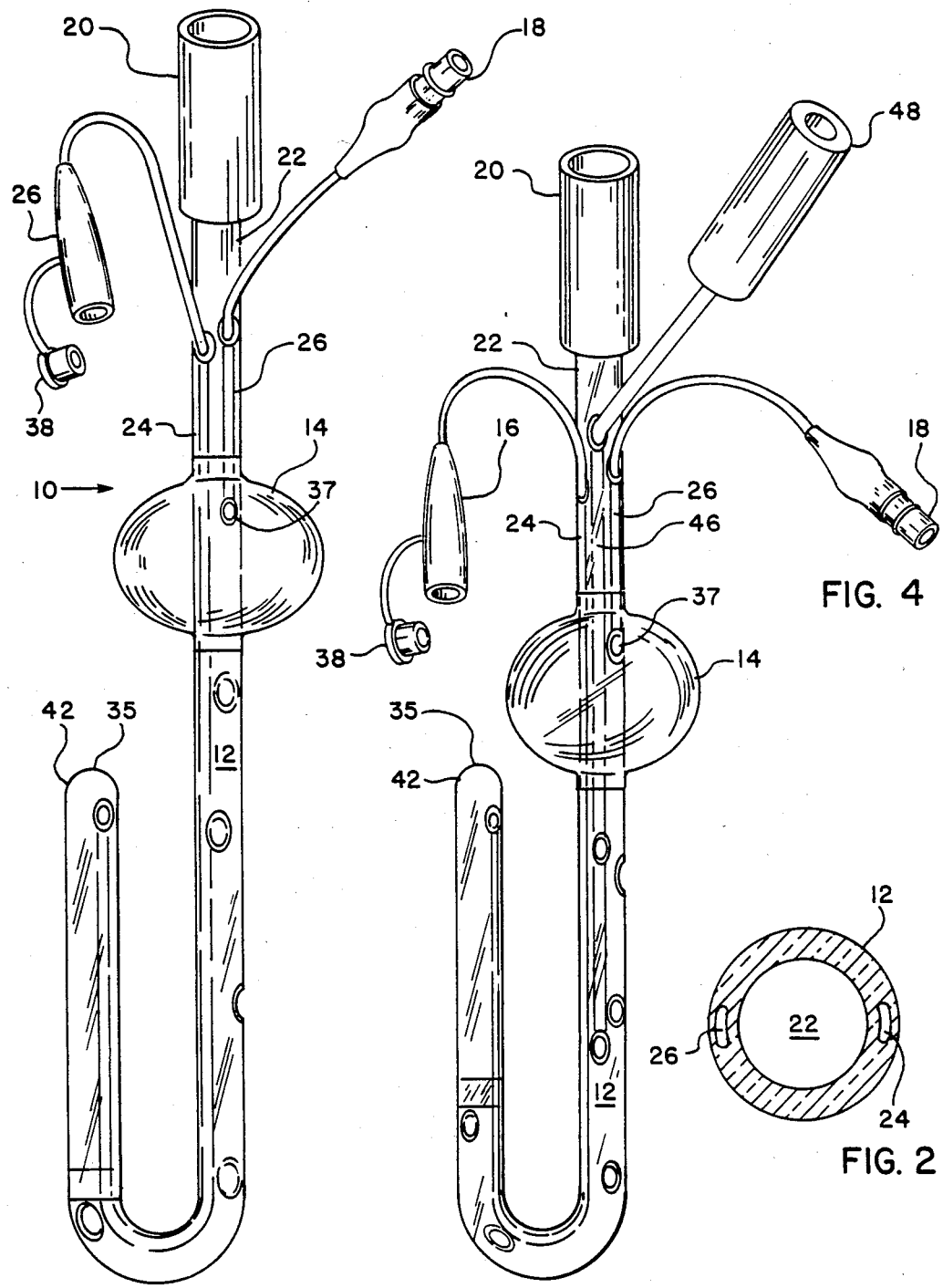

GASTROINTESTINAL FEEDING AND ASPIRATING DEVICE FOR USE IN TREATING PATIENTS

This application is a continuation-in-part, of application Ser. No. 312,125, filed 10/16/81, now abandoned.

BACKGROUND AND SUMMARY OF THE INVENTION

This invention relates to a gastrointestinal feeding and aspirating device and a method of use in treating patients.

Post-operatively, gastrointestinal functions usually deteriorate. The causes of this deterioration are varied and include such factors as the use of anesthesia or pain killing drugs, and the handling of the bowel during the operation. Additionally, air swallowed by the patient contributes to gastrointestinal malfunctions since the gas is inefficiently propelled through the digestive tract. This causes a problem commonly known as abdominal distention which not only impairs bowel function and interferes with the rate of absorption of nutrients through the bowel, but often prevents the patient from breathing deeply or coughing, which can lead to severe pulmonary difficulties. In severe cases, the pressure caused by the abdominal distention has been known to break open the patient's wound. One of the indirect effects of abdominal distention is the fact that due to the pain associated with it, and the lesser rate of bowel absorption, the patient often becomes undernourished which slows the healing process. It has, therefore, been a long-standing objective of the medical profession to prevent abdominal distention while providing sufficient nutrition in order to speed the patient's recovery.

One device which has been successful in handling these difficulties is a naso-esophago-gastric decompression tube with a duodenal feeding tube. I developed this nasal tube a number of years ago, and it is still available under my trademark G. MOSS, said tube being manufactured by National Catheter Company. This device has a number of aspirating orifices at the distal end of the esophagus. This is a very effective place to remove air since that passage is a small diameter conduit through which all the air must pass. While this naso-gastric tube has proved to be quite successful, there are a number of operations wherein a nasal tube cannot be used. Also, for various reasons, certain patients are unable to use a nasal tube.

When the nasal passageways cannot be used, an aspirating tube can be inserted directly through the abdominal wall and into the stomach. However, several difficulties are encountered when trying to aspirate the stomach. First, the stomach contains phlegm, which has a tendency to accumulate in the aspirating tube and the tube orifices causing blockages. Second, the stomach, when functioning, forms folds such that matter introduced into the stomach is divided and transported across the stomach within separate passageways. Since an aspirating orifice within the stomach can only lie within a single passageway, the aspiration is limited to matter passing through that passageway. Therefore, it is common for matter to bypass the aspirating orifices and proceed further along the digestive tract causing distention.

In addition to aspirating postoperatively, it is also important that the patient be provided with a sufficient amount of nutrition. This can be accomplished by passing a feeding lumen through the stomach and the pyloric sphincter into the proximal segment of the small bowel. A feeding solution introduced through the lumen will enter the proximal segment of the small bowel and be directed downstream through peristaltic action. When feeding a patient in this manner, the normal food paths are bypassed; thus, also avoiding the safeguards which warn of fullness. Therefore, one administering a solution in this manner must be aware of the possibility of overloading the small bowel. The possibility of overfeeding is increased when the malfunctioning gastrointestinal system affects the peristaltic action of the small bowel. The lack of peristaltic action prevents the downstream flow of food such that the feeding solution being introduced builds pressure within the bowel.

My first response to these difficulties was to use a gastrointestinal tube inserted through the abdominal wall which would work in a similar manner to my nasal tube. This involved directing the aspirating lumen up from the stomach to the distal end of the esophagus; thus, taking advantage of the small diameter conduit as had been done with the nasal tube. I soon found, however, that there was no practical way of securing the device in the needed position. While working on alternate methods to effect more complete aspirations, I realized that aspirating the proximal segment of the small bowel could serve a dual purpose when properly combined with a stomach aspirator. Since the proximal segment of the small bowel is also a small diameter conduit, most of the matter entering from the stomach would be aspirated. Additionally, when I used a single lumen with aspirating orifices in both the stomach and the proximal segment of the small bowel, I was able to take advantage of the natural digestive juices in the small bowel to dissolve the phlegm being aspirated upstream in the stomach. Thus, I was able to provide the additional aspiration needed to pick up matter missed in the stomach while also taking advantage of the body's own digestive juices to maintain the lumen free from blockages.

Aspirating the proximal segment of the small bowel also became an important aspect for the avoidance of overfeeding. My first experiments with this involved inserting two tubes through the stomach and the pyloric sphincter into the proximal segment of the small bowel, one tube for aspirating and the other for feeding. I positioned the feeding tube so that the feeding site would be downstream of the aspirating site. Since both the feeding and the aspiration were occurring beyond the pyloric sphincter, I found that any excess feeding solution could now flow quite easily retrograde and be aspirated. This not only prevents overfeeding, but it also warns the person administering that the bowel is not handling the feeding solution, so that he can regulate the rate accordingly.

It is, therefore, an object of this invention to provide an aspirating device which is effective in avoiding abdominal distention.

It is also an object of the invention to provide a device which is less subject to clogging than prior devices.

It is yet another object of this invention to provide a feeding and aspirating device which prevents overfeeding.

Briefly described, this invention consists of a tube having a feeding lumen and an aspirating lumen which are inserted into the patient's body and secured thereto. Both the aspirating lumen and the feeding lumen have orifices so as to communicate with various sites within the patient's body. When in its secured position, the feeding orifice is positioned in the proximal segment of the small bowel. Upstream from the feeding orifice, and before the pyloric sphincter, at least one aspirating orifice also communicates with the proximal segment of the small bowel. In the stomach, the same aspirating lumen has at least one additional orifice for aspirating the stomach.

In an alternate embodiment, the above invention has an additional lumen which has orifices therein which communicate solely with the stomach. This lumen acts as an additional source of aspiration for the stomach cavity and allows for the aspiration of that cavity without aspirating the proximal segment of the small bowel.

BRIEF DESCRIPTION OF DRAWINGS

FIG. 1 is an elevational view of a gastrointestinal feeding and aspirating device.

FIG. 2 is a cross-section through the lumens of the invention.

FIG. 4 shows the alternate embodiment of the invention where a fourth lumen is present.

DETAILED DESCRIPTION OF THE DRAWINGS

Figure 3:
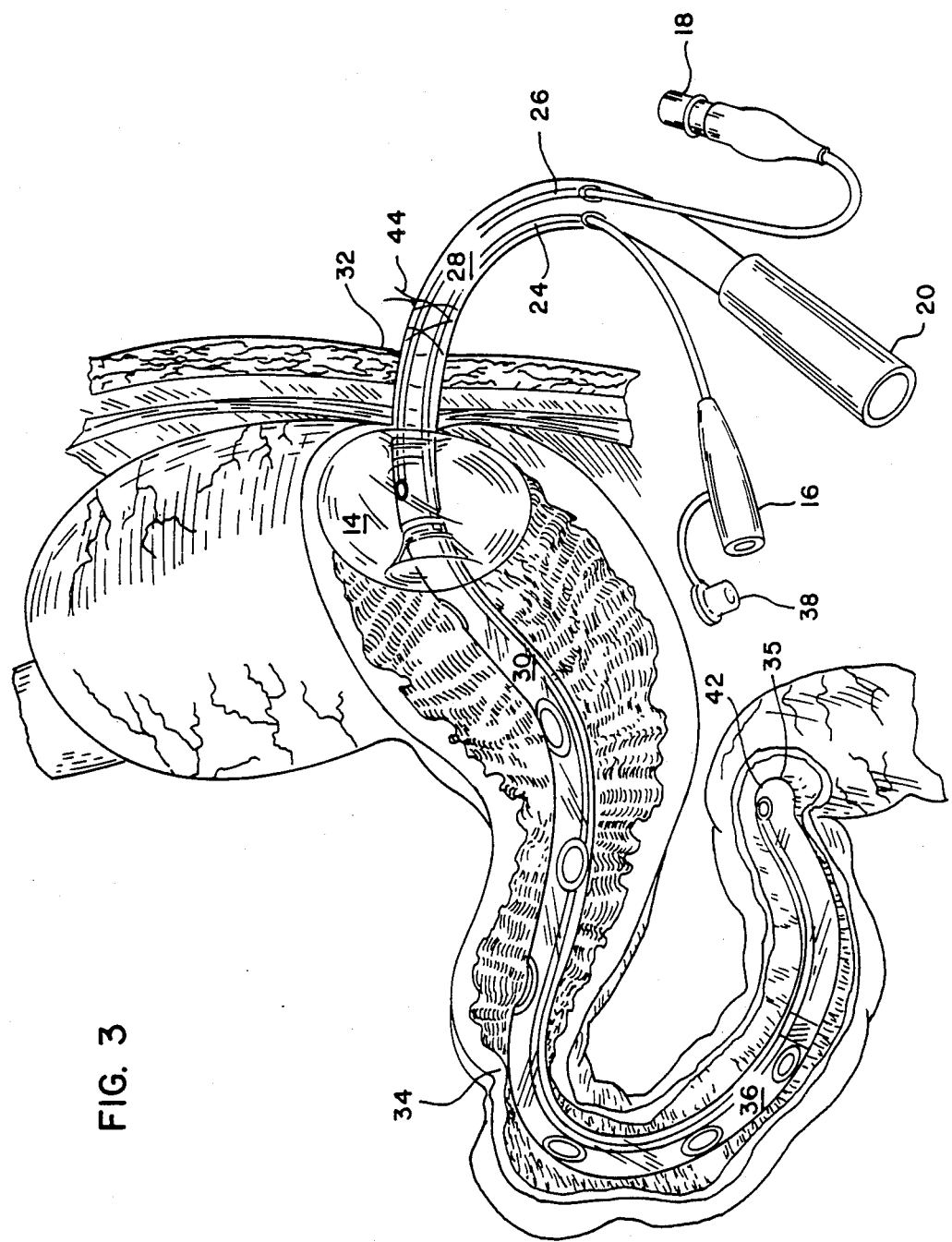
FIG. 3 shows the invention disposed in the patient's body.

As shown in FIG. 1, the gastrointestinal device 10 consists primarily of an elongated tube 12. Three lumens run through the tube. Toward one end of the tube, two lumens, which were in the tube, separate from the tube, thus leaving three individual lumens. There are three open-ended attachment members 16, 18 and 20, each of which is attached to one end of a lumen. Prior to this separation, a balloon 14 is circumferentially attached to the tube.

Since the device is used in conjunction with the internal organs of the body, it should be made of a bio-compatible material. I have found that both polysiloxane and polyurethane serve this purpose very well.

FIG. 2 shows the tube 12 in cross-section, revealing the three distinct lumens. The aspirating lumen 22, which is the largest of the three lumens, is centrally located. A feeding lumen 24 and an inflation lumen 26 are located 180° apart from each other on either side of the aspirating lumen. Each lumen communicates with the outside of the tube through at least one orifice.

FIG. 3 shows the gastrointestinal device positioned within the body. When so placed, several portions of the device can be described based upon their relationship to the anatomy. These portions are: the external end portion 28 which is outside of the body; the midportion 30 which extends from the body wall 32 to the pyloric sphincter 34; and the internal end portion 36 which extends from the pyloric sphincter to the internal end 35 of the device in the proximal segment of the small bowel.

Along these various portions are orifices each of which provides a passageway from a lumen to the outside of the tube. Externally, each lumen ends in an attachment such that the feeding attachment 16 corresponds to the feeding lumen 24; the inflation attachment 18 corresponds to the inflation lumen 26; and the aspirating attachment 20 corresponds with the aspirating lumen 22.

The aspirating attachment 20 at the external end of the aspirating lumen is adapted to connect to a source of suction. Orifices in the aspirating lumen are in the midportion and the internal end portion of the tube. Thus, both the stomach and the proximal segment of the small bowel are aspirated through the various orifices opening into aspirating lumen 22. The aspirating lumen is occluded three inches from the internal end of the tube 12.

The inflation attachment 18 at the external end of the inflation lumen 26 is adapted to receive a syringe. The inflation orifice 37 in the tube communicates with the inside of the balloon 14. Thus, the balloon can be inserted into the body in its deflated position and then, as shown in FIG. 3, can be inflated just inside the stomach.

The feeding attachment 16, which is located at the external end of the feeding lumen 24 is adapted to receive a male luer fitting. Connected to the feeding attachment is a sealing cap 38 which serves to close the external end of the lumen when it is not in use. The feeding lumen travels almost the entire length of the tube 12, ending at a feeding orifice in the side of the tube. This opening is in the side of the tube in order to enable the internal end 35 of the tube to have a rounded tip 42 which facilitates insertion. In the preferred embodiment of this invention, the feeding orifice is three inches closer to the internal end than the last aspirating orifice.

The separation of the orifices such that the feeding orifice is 3 inches closer to the internal end or downstream from the last aspirating orifice allows the patient's system to absorb the maximum amount of nourishment it can handle while aspirating any amount of overfeeding before the functioning of the system is compromised.

This separation is critical to the safe and effective operation of the feeding and aspirating device. Peristaltic activity along about 3 inches (7-8 cm) of intestine prevents spontaneous retrograde flow, acting in effect as a "one-way valve". When feeding rates are not excessive to the patient's gastrointestinal function, the separation prevents inadvertent loss of nourishment. However, should the patient be overfed, only the excess will flow retrograde with a virtually unmeasurable pressure increase within the system and be withdrawn through the aspirating orifice. Thus, the patient absorbs the maximum his impaired function will permit while gastrointestinal function will not deteriorate since excess distal feeding solution does not develop physiologically detrimental pressure as would be the case if significantly greater retrograde flow was required to accomplish aspiration.

The amount of pressure necessary to achieve retrograde flow of about 3 inches will vary slightly according to the size of the medical patient being treated. For example, when treating a child or infant the "one-way valve" effect may be accomplished with only 2 inches of intestine. Therefore, with a 3 inch separation of the feeding and aspirating orifices the pressure increase in the system would be greater, though still not physiologically detrimental, in order to produce retrograde flow to the last aspirating orifice. Conversely, if a large medical patient is being treated a complete "one-way valve" effect may require 4 inches of intestine. In this case, the 3 inch separation would be traversed with less pressure than normally required. Nevertheless, the separation would be sufficient to allow the patient to absorb virtually the maximum amount of nourishment that his impaired function would permit.

Due to the difference in the size of medical patients, the distance between the aspirating and feeding orifices can range from 2-4 inches. Although, as previously stated, 3 inches is preferred since it can be used for all patients, where the application of such a tube is appropriate, without loss of nourishment or compromising the patient's system should overfeeding occur.

Procedurally, the internal end of this device is pulled through a stab wound which is made in the abdominal wall. A perforation is then made in the stomach wall, and the internal end is carefully inserted. The rounded tip 42 is than advanced out from the stomach, into and down the intestine until a balloon 14 fully enters the stomach. The balloon is then inflated with 10-30 ml of sterile water. Slight traction is applied to the external portion of the device, sandwiching the stomach wall between the balloon and the abdominal wall. The device is then anchored with a suture 44 to the abdominal skin at the point of exit, as shown in FIG. 3.

In operation, the suction aspirates both the stomach and the proximal segment of the small bowel. The body deposits a large amount of digestive juices into the small bowel and, therefore, the aspiration of the bowel draws these juices through the aspirating lumen which keeps the lumen clear. To feed the patient, a feeding solution is administered through the feeding lumen 24 and exits through the feeding orifice at the internal end 35 of the tube 12. Should an excess amount of feeding solution be administered to the patient, it will flow retrograde to the aspirating orifices in the proximal segment of the small bowel, thus preventing overfeeding.

FIG. 4 shows an alternate embodiment of this invention wherein an additional lumen is used for the sole purpose of aspirating the stomach. This stomach aspirating lumen 46 has an external end portion. Attached to the external end is an aspirating fitting 48 which is opened and adapted to be connected to a source of suction. The stomach aspirating lumen has orifices which communicate with the stomach through the mid-portion 30 of the tube 12. This stomach aspirating lumen is occluded prior to reaching the internal end portion of the tube.

Changes and modifications in the specifically described invention can be carried out without departing from the scope of the invention which is intended to be limited only by the scope of the appended claims.

What is claimed:

1. A gastrointestinal feeding and aspirating device for surgical insertion into a patient's body through the abdominal and gastric wall, comprising:
    an aspirating lumen having an external end portion to be disposed outside the body, said external portion having an opening for connection to a source of suction and having an internal end portion to be disposed in the proximal segment of the small bowel, said portion having at least one orifice for intake of matter to be discharged from the body;
    a feeding lumen having an external end portion to be disposed outside the body, said external portion having an opening adapted to receive food to be transported through the lumen and having an internal end portion to be disposed in the proximal segment of the small bowel, said internal portion having an orifice therein for the discharge of food; and
    means for securing the device to the patient's body through the abdominal and gastric wall such that the internal portion of each lumen is located in the proximal segment of the small bowel, said feeding orifice being maintained at a location which is substantially three inches downstream of the most distal aspirating orifice, the portion of each lumen between the securing means and that lumen's external opening being continuous.

2. The invention of claim 1 wherein said securing means further comprises:
    an inflatable member securely attached to the device to be disposed within the body; and
    an inflation lumen having an external end portion to be disposed outside the body and an inflation orifice communicating with the interior of the inflatable member, so that the inflatable member can be directed into the body while deflated and then inflated from outside of the body.

3. The invention of claim 2 wherein the device is made of polysiloxane.

4. The invention of claim 2 wherein the device is made of a material which is bio-compatible with the body.

5. The invention of claim 4 wherein the device is made of polyurethane

6. The invention of claim 4 wherein the lumens are bundled together in order to form one unitary gastrointestinal tube device.

7. The invention of claim 6 wherein the feeding lumen extends beyond the internal end of the aspirating lumen, the feeding orifice is an opening on the side of the interior end portion of the feeding lumen and the internal end of the tube device is closed and rounded.

8. The invention of claim 7 wherein the external end portion of the feeding lumen is adapted to receive a male luer fitting.

9. The invention of claim 8 wherein the inflation lumen and the feeding lumen are disposed on opposite sides of the aspirating lumen so as to be 180° apart from each other.

10. The invention of claim 4 further comprising:
    an additional stomach aspirating lumen having an external end portion to be disposed outside the body, said external portion having an opening for connection to a source of suction and having an internal end portion to be disposed in the stomach, said internal portion having at least one orifice for intake of matter to be discharged from the body.

11. The invention of claim 1 wherein the feeding orifice is downstream from the last aspirating orifice by a range of 2-4 inches.

12. A gastrointestinal feeding and aspirating device for surgical insertion into a patient's body through the abdominal and gastric walls, comprising:
    an aspirating lumen having an external end portion to be disposed outside the body, said external portion having an opening for connection to a source of suction and having an internal end portion to be disposed in the proximal segment of the small bowel, and a mid-portion adjacent to the internal end portion to be disposed in the stomach, said internal end portion and said mid-portion each having at least one orifice for intake of matter to be discharged from the body;
    a feeding lumen having an external end portion to be disposed outside the body, said portion having an opening adapted to receive food to be transported through the lumen and having an internal end portion to be disposed in the proximal segment of the small bowel, said internal portion having an orifice therein for the discharge of food; and means for securing the device to the patient's body through the abdominal and gastric walls such that the internal end portions of the aspirating lumen and the feeding lumen are located in the proximal segment of the small bowel, and said mid-portion of the aspirating lumen is located in the stomach, said feeding orifice being maintained at a location which is substantially three inches downstream of the most distal aspirating orifices, the portion of each lumen between the securing means and the lumen's external opening being continuous.

13. The invention of claim 12 wherein the feeding orifice is downstream from the last aspirating orifice by a range of 2–4 inches.

* * * * *